United States Patent [19]
Funnell

[11] Patent Number: 5,383,471
[45] Date of Patent: Jan. 24, 1995

[54] SURGICAL BIOPSY INSTRUMENT

[76] Inventor: David M. Funnell, 19 Westcott Rd., Hopedale, Mass. 01747-1824

[21] Appl. No.: 107,331

[22] Filed: Aug. 16, 1993

Related U.S. Application Data

[63] Continuation of Ser. No. 866,430, Apr. 10, 1992, abandoned.

[51] Int. Cl.⁶ ............................................. A61B 10/00
[52] U.S. Cl. ................................. 128/751; 606/170; 606/174; 606/207
[58] Field of Search ................. 128/749, 751; 606/167, 606/170, 171, 174, 205, 206, 207, 208; 30/173, 182, 186, 187, 134, 135, 355, 353; 254/28

[56] References Cited

U.S. PATENT DOCUMENTS

| | | | |
|---|---|---|---|
| 540,092 | 5/1895 | Farish | 30/134 |
| 1,127,948 | 2/1915 | Wappler | 128/7 |
| 2,940,727 | 6/1960 | Segal | 254/28 |
| 3,895,636 | 6/1975 | Schmidt | 606/205 |
| 4,200,111 | 4/1980 | Harris | 128/751 |
| 4,351,210 | 9/1982 | McKindary | 83/835 |
| 4,483,562 | 11/1984 | Schoolman | 294/19.1 |
| 4,669,470 | 6/1987 | Brandfield | 606/174 |
| 4,669,471 | 6/1987 | Hayashi | 606/205 |
| 4,712,545 | 12/1987 | Honkanen | 606/184 |
| 4,721,116 | 1/1988 | Schimtgon | 128/751 |
| 4,763,669 | 8/1988 | Jaeger | 128/751 |
| 4,771,540 | 9/1988 | LaBounty | 30/134 |
| 4,815,460 | 3/1989 | Porat et al. | 606/207 |
| 4,815,476 | 4/1989 | Clenick | 128/751 |
| 4,881,550 | 11/1989 | Kothe | 128/752 |
| 4,887,612 | 12/1989 | Esser et al. | 128/751 |
| 4,896,678 | 1/1990 | Ogawa | 128/751 |
| 4,957,500 | 9/1990 | Liang et al. | 606/157 |
| 4,976,723 | 12/1990 | Schad | 606/170 |
| 5,011,491 | 4/1991 | Boenko et al. | 606/207 |
| 5,085,404 | 2/1992 | Thieleke et al. | 254/28 |
| 5,090,662 | 2/1992 | Koo | 254/28 |
| 5,133,727 | 7/1992 | Bales et al. | 606/170 |

FOREIGN PATENT DOCUMENTS 0316816 11/1988 European Pat. Off. .

Primary Examiner—Stephen C. Pellegrino
Assistant Examiner—Guy V. Tucker
Attorney, Agent, or Firm—Pandiscio & Pandiscio

[57] ABSTRACT

A surgical instrument useful as a biopsy tool and other related cutting or manipulating apparatus having two or more complementary mating jaws for securing and cutting the selected tissue, pivoted and operable remote from the operator handle. The surgical instrument includes elements to prevent the relative dislocation, or 'racking', of the cutting elements when the instrument is rotated on an axis perpendicular to the pivot point of the jaws. Further features of the present invention include an asymmetric continuous cutting surface about the major portion of the perimeter of the jaws, and a protruding tip of each of the jaw cutting surfaces, forming an incisor-like cutting region to insure that the sampled tissue is secured within the region of the jaw and cleanly cut free from the surrounding tissue. When fully engaged, the surgical instrument encloses the sample to be removed. The anti-racking structure is adaptable to other surgical instrument functions as may be applied to laparoscopic surgery, wherein the other surgical elements replace the forward cutting surfaces.

16 Claims, 3 Drawing Sheets

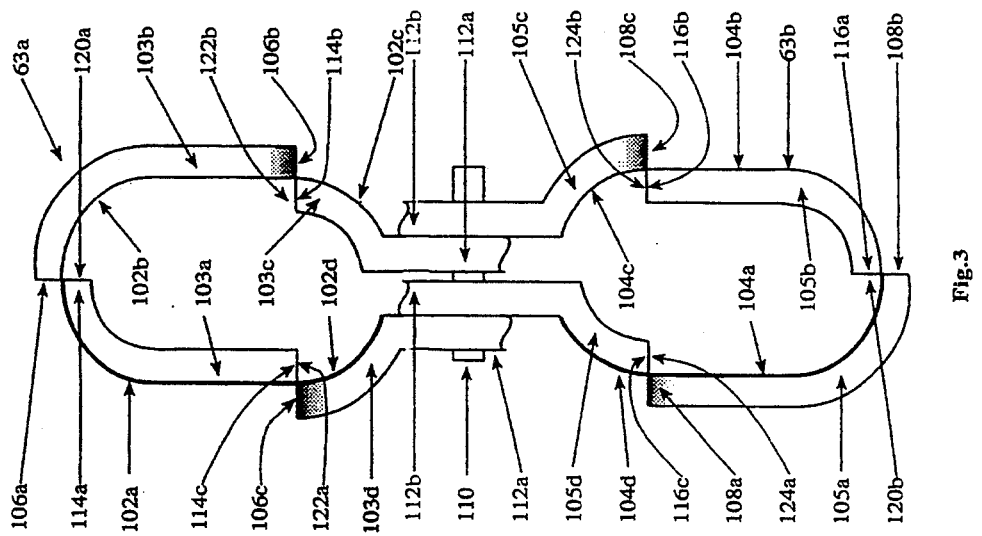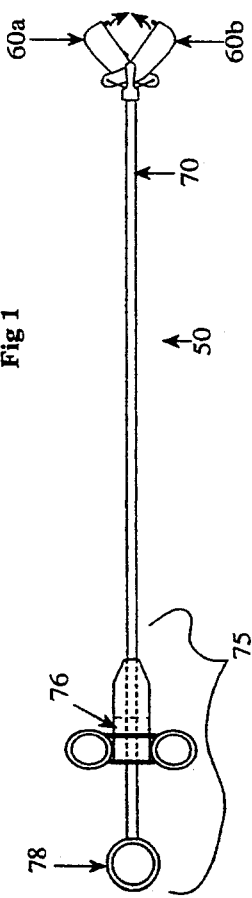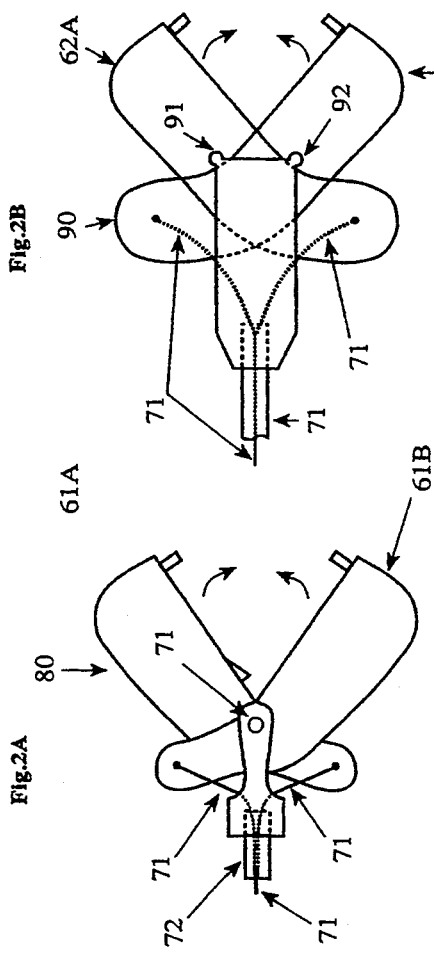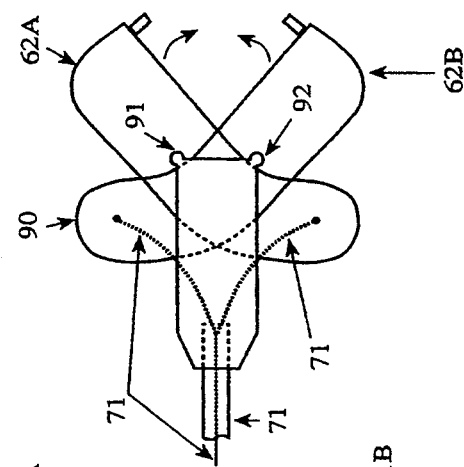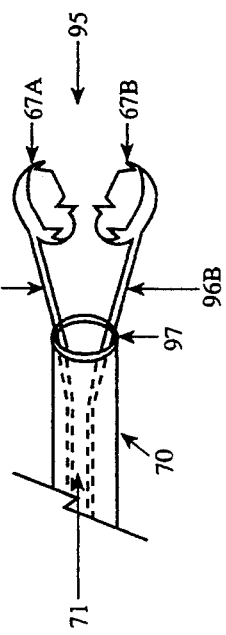

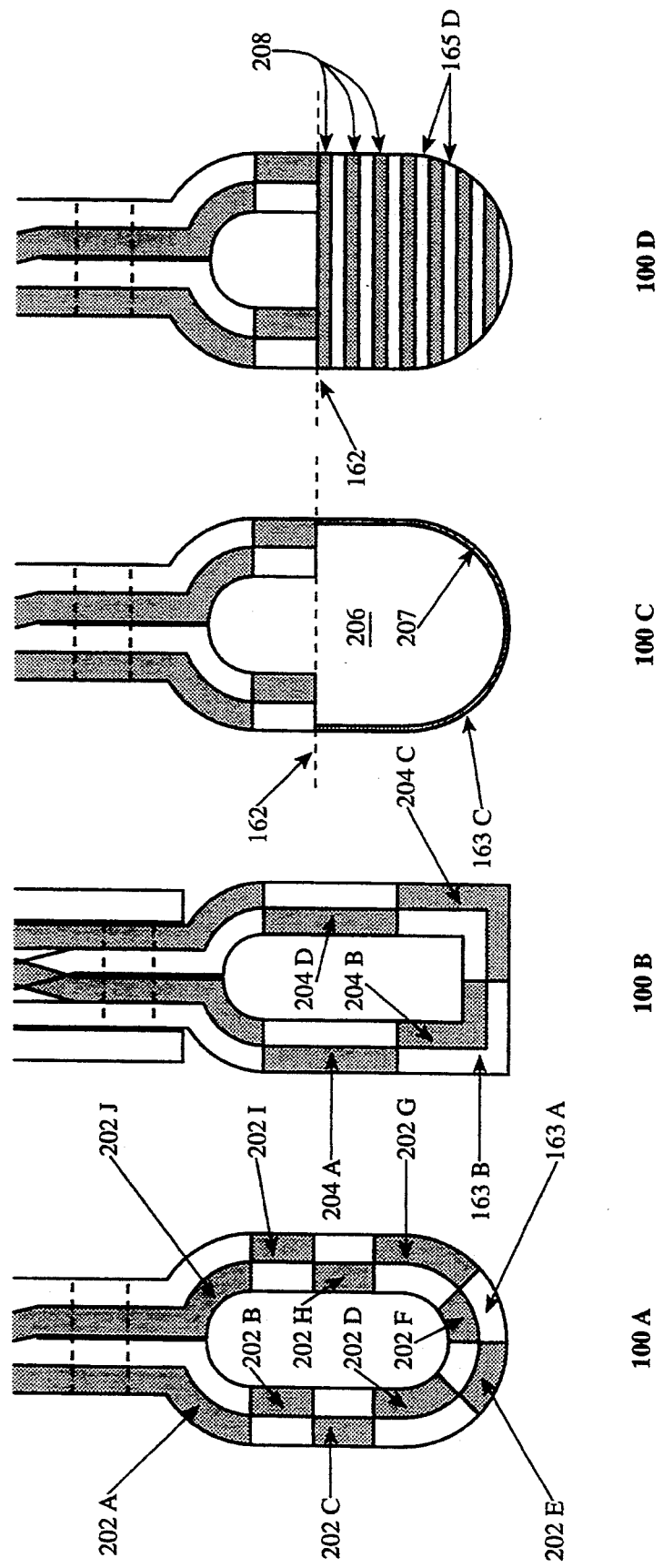

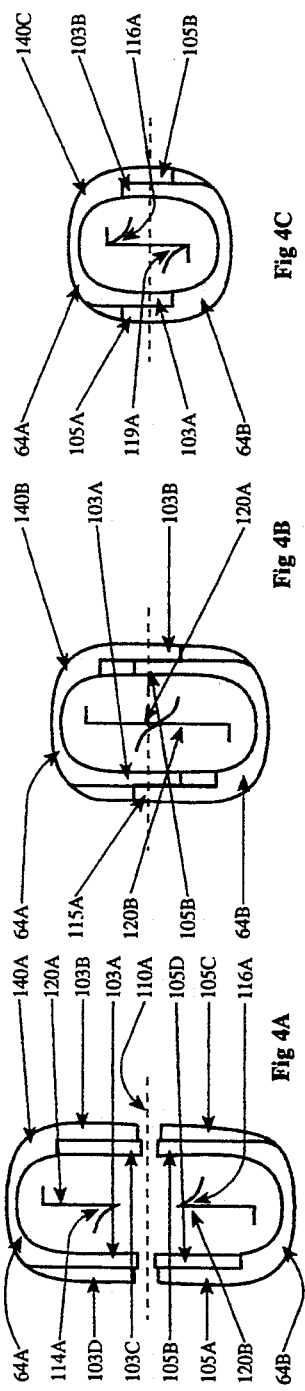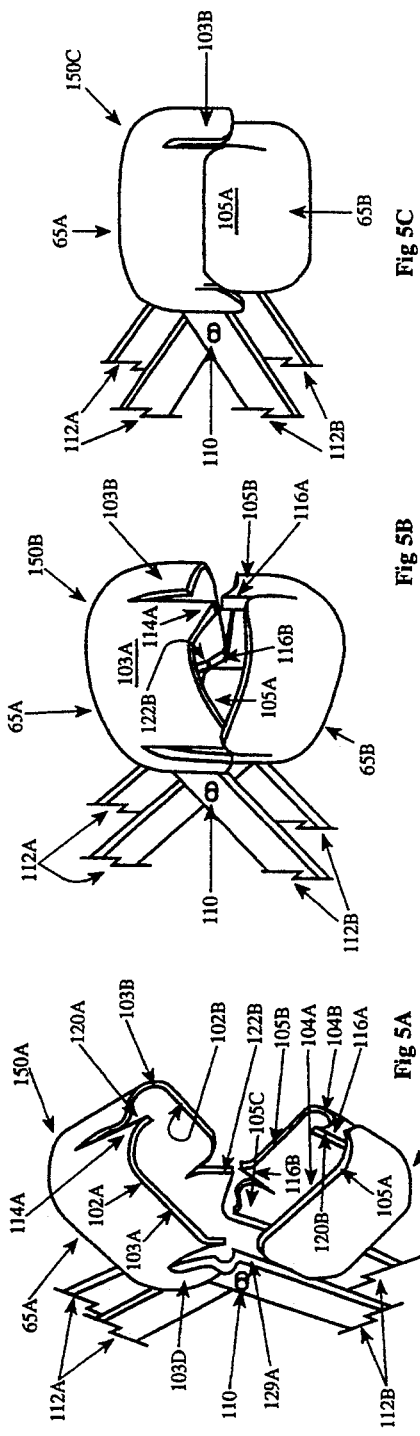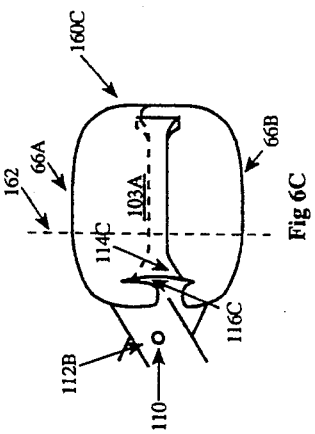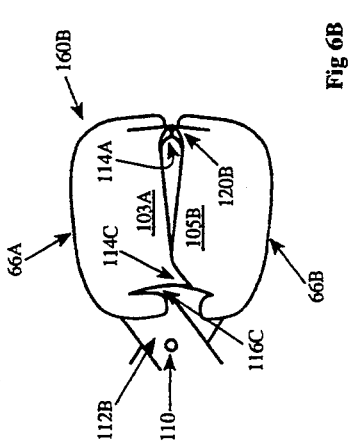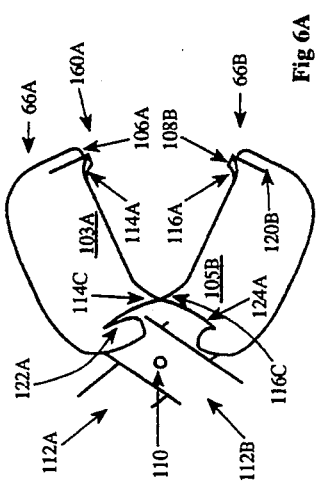

SURGICAL BIOPSY INSTRUMENT

This is a continuation of copending application Ser. No. 07/866,430 filed on Apr. 10, 1992, now abandoned.

FIELD OF THE INVENTION

The present invention relates to surgical instruments, and in particular to surgical instruments useful in biopsy and laparoscopic procedures.

BACKGROUND OF THE INVENTION

Cutting instruments such as scissors and punches, and certain forceps have precisely aligned jaws which pivot to each other to provide the desired function, which if misaligned, severely reduces the performance of the tool, and if severe enough, causes damage if not complete destruction of the tool. Frequently, such pivoted cutting or clamping elements are mounted at the end of an operating rod or shaft, distal from the operator handle. Typically, when the working surfaces are experiencing difficulty, the operator twists the instrument by applying additional force to the cutting or clamping jaws via the handle, and also applies a torsion along the axis of the handle which is applied to the cutting or clamping jaws via the pivot point of the jaws. Moreover, when the jaws become misaligned through normal use, such misalignment often results in the instrument self-destructing.

The primary response of instrumentation manufacturers to minimize the problem of tip misalignment is to increase the relative size of the pivot points, which results in only a limited improvement in maintaining jaw tip alignment as the instrument is rotated or otherwise abused by the operator.

Moreover, cutting instruments such as scissors and punches typically have a continuous cutting surface to engage the tissue. The continuous cutting surface must be precisely aligned to provide optimal cutting, and further increases the necessity of the aforementioned tip alignment to provide optimal, if not useful instrument operation.

Furthermore, the amount of tissue which is excised by the cutting tool, or grasped by the jaws is largely determined by the effectiveness of the tip or most distal end of the cutting surfaces to engage the tissue, which is typically continuous with the adjacent perimeter portions of the jaw. However, the effectiveness of the continuous tip to engage the tissue is severely limited, and is further reduced as the tip becomes dull through use or misalignment.

SUMMARY OF THE INVENTION

The surgical instrument according to the present invention provides confronting and sliding surfaces forward or distal of the pivot point, to provide an antiracking cutting or clamping tool which maintains the tool tips in alignment despite shear forces applied to the tips by a translated rotational force applied to the instrument along the axis perpendicular to the pivot, as may be provided through operator abuse.

Furthermore, the present invention comprises complimentary asymmetrical or symmetrical bifurcated cutting jaws which are self aligning and reduce the requirement of precise hinge or pivot tolerance and alignment. The combined cutting surface formed by the mutual operation of the jaws is substantially continuous throughout the circumference of the cutting tool opening, while the cutting surface on each of the jaws is discontinuous.

Furthermore, tissue engagement via the tip of the jaws is significantly enhanced with the addition of protruding ends of the discontinuous cutting surfaces, which form an incisor-like cutting point to securely grasp the tissue in advance of the remaining jaw cutting surfaces as the jaws are moved together.

BRIEF DESCRIPTION OF THE DRAWING

These and other features of the present invention will become more readily understood, or rendered obvious, upon a reading of the following detailed description, and upon an examination of the drawings, in which similar parts are identified by like reference numerals.

FIG. 1 is a side view of one embodiment of the present invention mounted on an elongated control arm;

FIG. 2A and FIG. 2B are embodiments of the present invention as affixed to the control arm, having one and two pivot points respectively;

FIG. 2C is an embodiment of the present invention having a sliding, non-pivoting jaw closure;

FIG. 3 is a plan view of the cutting surfaces of the jaws according to one embodiment of the present invention;

FIG. 3A–3D are plan views of the jaws according to alternate embodiments of the present invention;

FIG. 4A. 4B and 4C are pictorial representations of the cutting surfaces of the jaw according to the present invention from a frontal view;

FIGS. 5A, 5B, 5C are perspective drawings showing one embodiment of the present invention in the open, partially closed, and closed position; and FIGS. 6A, 6B and 6C are partial side views of one embodiment of the present invention showing the relative engagement of the cutting surfaces for an open, partially closed, and closed relative position of the jaws.

DETAILED DESCRIPTION OF THE INVENTION

The general configuration of surgical instrument 50 embodying the present invention wherein jaws 60A and 60B are connected to a control cable 70 having concentric operating members therein which are connected in turn to a control handle 75 including an outer concentric member 76 connected to the inner member of the control cable 70, and a handle inner member 78 connected to the control cable 70 external member, wherein the jaws 60A and 60B are closed with the movement of the control handle elements 76 and 78 together.

One and two pivot embodiments 80, 90 respectively, are shown in FIGS. 2A and 2B. The jaws 61A and 61B are moveable about a single pivot point 81 which is rigidly affixed to the outer member 72 of the control cable 70. As shown in FIG. 2B, in a two pivot embodiment, the pivot points 91 and 92 are rigidly affixed to the outer member 72 of the control cable 70. The jaw 62A is connected so as to pivot about point 91, and the jaw 62B is connected so as to pivot about point 92. The control cable inner member 71 is connected to the lever (proximal) ends of the jaws 62A and 62B. The jaws 61A and 61B are caused to move together as the center element 71 of the control cable 70 is withdrawn relative to the cable outer portion 72, which is connected to the proximal end of each jaw 61A and 61B. In the embodiment of the present invention having two pivot points 91 and 92 is shown in FIG. 2B, wherein the jaws 62A and 62B are moveable relative to each other when pivoted on pivot points 91 and 92 respectively. As the center portion 71 of the control cable 70 is withdrawn relative to the exterior member 72 of the control cable 70, the jaws 62A and 62B are moved towards each other.

A no-pivot embodiment 95 is provided in FIG. 2C, wherein jaws 67A, 67B are closed as center portion 71 of the cable 70 causes the arms 96A, 96B to be drawn against the end 97 of the exterior member of the control cable 70.

A plan view 100 of the confronting cutting surfaces of the jaws 63A and 63B according to one embodiment of the present invention is shown in FIG. 3. The jaw 63A includes a discontinuous cutting surface including portions 102A, 102B, 102C and 102D. The jaw 63B provides a complementary asymmetric jaw structure comprising a discontinuous cutting surface including portions 104A, 104B, 104C and 104D which mate in close proximity with the respective portions 102A, 102B, 102C and 102D when the taws 63A and 63B are moved towards one another about the pivot 110. In the embodiment shown in FIG. 3, the end surfaces 106A, 106B and 106C, as well as the cutting surface portions 102B and 102D of jaw 63A, are generally rounded downwardly into the plane of the drawing. Similarly, the end surfaces 108A, 108B and 108C, as well as the cutting surface portions 104A and 104C of jaw 63B, are generally rounded downwardly into the plane of the drawing. The end surfaces 114A, 114B and 114C, as well as the cutting surface portions 103A and 103C of jaw 63A, are raised upward and extend outward of the plane of the drawing. Similarly, the end surfaces 116A, 116B and 116C, as well as the cutting surface portions 105B and 105D of jaw 63B, are raised upward and extend outward out of the plane of the drawing. As a result of this construction, as the jaws 63A and 63B are pivoted towards one another on the pivot 110, the cutting surface 120A formed on the raised end surface 114A of jaw 63A, and the cutting surface 120B formed on the raised end surface 116A of jaw 63B, slide upon one another. In a similar manner, a pair of complementary slidable cutting surfaces 122A and 124A are provided by the ends of the cutting members 103A and 105D, respectively; and a pair of complementary slidable cutting surfaces 122B and 124B are provided by the ends of the cutting members 103C and 105B, respectively.

The cutting surfaces 102A and 102C are formed along the exterior edge of internal cutting members 103A and 103C; similarly, the cutting surfaces 104B and 104D are on the exterior edge of internal cutting members 105B and 105D of jaw 63B. The cutting surface 102B and 102D are formed on the interior edge of the exterior cutting member 103B and 103D of jaw 63A; similarly, the cutting surface 104A and 104C are formed on the interior edge of exterior cutting members 105A and 105C of jaw 63B. The jaws 63A and 63B are connected to lever arms 112A and 112B respectively and are relatively moveable about the pivot 110. The lever arms 112A and 112B each comprise a pair of lever arms spaced apart on said pivot to economically provide further structural integrity.

As can be seen in FIG. 3, internal cutting members 103A and 103C are laterally offset from exterior cutting members 103B and 103D. Cutting surfaces 102A, 102B, 102C and 102D, however, are substantially continuous when viewed from the position shown in FIG. 3 in that there is no lateral offset.

A plan view 100A of a jaw 163A according to an alternate embodiment is shown in FIG. 3A, including a greater number of cutting members 203A, 202B, 202C, 202D, 202E, 202F, 202G, 202H, 202I and 202J. A plan view 100B of a jaw according to a further embodiment is shown in FIG. 3B having parallel cutting members 204A, 204D and right-angled cutting members 204B, 204C.

Three simplified drawings 140A, 140B and 140C showing a partial cross section of one embodiment of the present invention in various stages of engagement of the jaws 64A and 64B is shown in FIGS. 4A, 4B, and 4C. As illustrated in FIGS. 4A–4C, the incisor-like protrusions 114A and 116A extend towards each other, presenting confronting and relatively slidable surfaces 120A and 120B. With the jaws 64A and 64B open in FIG. 4A, the tips of the protrusions 114A and 116A do not meet, and the cutting members 103A–103D and 105A–105D do not meet. As the jaws 64A and 64B are brought into a partially closed position as illustrated by FIG. 4B, the cutting member 103A and its complementary cutting member 105A, as well as the cutting member 103B and its complementary cutting member 105B, engage tissue (not shown). At the same time, the tips of the incisor-like protrusions 114A and 116A (see FIG. 4A) pierce the tissue, thus allowing the confronting surfaces 120A and 120B to slide relative to one another through the tissue.

As the jaws 64A and 64B are completely closed, as shown in FIG. 4C, the cutting surfaces discussed above are fully engaged as are the protrusions 114A and 116A and the sliding surfaces 122A, 124A and 122B, 124B (not numbered or illustrated in FIG. 4C for the sake of clarity, but indicated in FIG. 3).

Perspective drawings 150A, 150B and 150C showing an opened, partially closed and closed position of one embodiment of the present invention are shown in FIGS. 5A, 5B and 5C. As can be observed in FIGS. 5A–5C, the inner cutting members 103A and 105B are obscured by overlapping outer cutting members 105A and 103B when the jaws are in a completely closed position.

Simplified longitudinal cross sectional drawings 160A, 160B and 160C, showing one embodiment of the present invention in an open, partially closed, and closed position is shown in FIGS. 6A, 6B and 6C respectively. The anti-racking feature of the present invention can be appreciated by observing the sliding and overlapping motion of surfaces 122A and 124A of protrusions 114C and 116C respectively as the jaws 66A and 66B move from an open to a closed position, FIGS. 6A–6C. Thus according to the present invention as the cutting surfaces and the incisor-like protrusions 114A and 116A engage the tissue forward of the pivot 110, the intervening sliding surfaces 122A and 124A, as well as the surfaces 122B and 124B (not shown in FIGS. 6A, 6B and 6C, but indicated in FIG. 3 with respect to similar jaws 63A and 63B), engage, providing structural reinforcement of the jaws 66A and 66B allowing such to remain in precise alignment as the jaws are brought to a closed position.

The scope of the present invention includes further embodiments wherein the frontal portion of the jaws forward of dotted line 162 (distal from the pivot 110) is replaced with other surgical tip functions which require similar precise alignment, as may be applied to surgical procedures other than biopsy removal, such as laparoscopic surgery. Exemplary devices are shown in plan views 100C and 100D of FIG. 3C and FIG. 3D. The continuous edge 207 defines an enclosed volume 206, and ridges 208 form corrugated surfaces which grip tissue when each jaw mates with a complementary confronting jaw (not shown). Accordingly, the present invention includes the attachment of such surgical devices forward to provide a surgical instrument including the anti-racking structure having sliding surfaces 122A, 124A and 122B and 124B. Moreover, implementations embodying the dual pivot of FIG. 2B would provide the curved surfaces 122A, 124A and 122B, 124B having the appropriate curvature to mate and provide a transmission of force between as the jaws are brought to a full closed position. Further modifications and substitutions made by one of ordinary skill in the art is considered to be within the scope of the present invention, which is not to be limited except by the claims which follows:

What is claimed is:

1. An apparatus for use in cutting and removing a selected tissue sample from a tissue mass, said apparatus comprising:

a first jaw having a rear portion and a front portion, and including at least two cutting members, each cutting member having an interior and an exterior surface, the first cutting member extending from the rear portion of the jaw towards the front portion of the jaw but terminating at a forward short of said front portion, a cutting edge of said first such cutting member being formed on its exterior surface, the second cutting member being located so that it extends from next adjacent the forward end of said first cutting member towards the front portion of the jaw, a cutting edge of the second cutting member being formed on its interior surface, said cutting members being disposed in laterally offset relationship to one another with their respective cutting edges being aligned so as to form a substantially continuous first cutting surface without a lateral offset;

a second jaw having a rear portion and a front portion, and including at least a third and a fourth cutting member, each cutting member having an interior and an exterior surface, the third cutting member extending from the rear portion of the second jaw towards the front portion of the second jaw but terminating at a forward end short of said front portion, a cutting edge of said third cutting member being formed on its interior surface, the fourth cutting member being located so that it extends from next adjacent the forward end of said third cutting member towards the front portion of the second jaw, a cutting edge of the fourth cutting member being formed on its exterior surface, said third and fourth cutting members being disposed in laterally offset relationship to one another with their respective cutting edges being aligned so as to form a substantially continuous second cutting surface without a lateral offset; and means for moving at least one of said jaws towards the other jaw so that the respective cutting edges on said first and second jaws may be repositioned from a first position in which the cutting edges forming the first cutting surface are completely disengaged from the cutting edges forming the second cutting surface, to a second position wherein the cutting edges comprising the first cutting surface are fully in engagement with the cutting edges comprising the second cutting surface, and wherein as said cutting edges are progressively moved from said first into said second position, the exterior surface on the first cutting member of said first jaw confronts and then engages the interior surface on the juxtaposed third cutting member of said second jaw, and the interior surface on the second cutting member of said first jaw confronts and then engages the exterior surface on the juxtaposed fourth cutting member of said second jaw, the engagement of said cutting surfaces proceeding in a progressive fashion from no engagement at an open jaw position to maximum engagement at a closed jaw position, whereby racking of the cutting members is prevented as soon as the cutting edges on the first and third cutting members begin to become engaged while said jaws are still partially open, and the anti-racking ability of said apparatus continues to increase as the second and fourth cutting members are progressively engaged and said jaws are brought towards the closed jaw position.

2. The apparatus of claim 1 wherein said first jaw and said second jaw include a plurality of cutting members which are arranged so that they extend from the rear portion to the front portion of said jaws so as to define a substantially enclosed volume when said jaws are fully closed.

3. The apparatus of claim 2 wherein the cutting edges forming the first and second cutting surfaces are arranged to form at least three sides of a generally rectangularly shaped area.

4. The apparatus of claim 1 wherein at least some of the juxtaposed cutting edges on said first and second jaws are formed as curved cutting surfaces.

5. The apparatus of claim 1 wherein at least one of said jaws includes a cutting tooth extending from the interior of said at least one jaw towards the interior of the other jaw when said jaws are in said engaged position.

6. The apparatus of claim 1 further comprising:

a first lever arm having a distal end and a proximal end, said first lever arm being connected to and disposed at an angle with respect to said first jaw;

a second lever arm having a distal end and a proximal end, said second lever arm being connected to and disposed at an angle with respect to said second jaw; and pivot means for connecting said proximal ends of said first and second lever arms in such manner that the interior and exterior surfaces on the cutting members of the first jaw matingly engage in a sliding relationship with the respective juxtaposed exterior and interior surfaces on the cutting members of the second jaw as said cutting surfaces are repositioned from said first towards said second position.

7. The apparatus of claim 6 further comprising activation means attached to the proximal ends of said lever arms for moving the distal ends of said first and second lever arms towards and away from one another.

8. The apparatus of claim 1 further comprising:

a first lever arm having a distal end and a proximal end, said first lever arm being connected to and disposed at an angle with respect to said first jaw;

a second lever arm having a distal end and a proximal end, said second lever arm being connected to and disposed at an angle with respect to said second jaw; and first and second pivot means connecting said proximal ends of said first and second lever arms in such manner that the interior and exterior surfaces on the cutting members of the first jaw matingly engage in a sliding relationship with the respective juxtaposed exterior and interior surfaces on the cutting members of the second jaw as said cutting surfaces are repositioned from said first towards said second position by rotating said jaws about said first and second pivot means.

9. An apparatus for use in cutting and removing a selected tissue sample from a tissue mass, said apparatus comprising first and second jaws, each jaw including means for engaging tissue;

said first jaw having a rear portion and a front portion, and including at least a first pair of cutting members and a second pair of cutting members, each cutting member having an interior and an exterior surface, the first pair of cutting members being so arranged that a member thereof is located on each side of the longitudinal axis of said first jaw, said first pair of cutting members extending from the rear portion of the first jaw towards the front portion thereof, but terminating at a forward end short of said front portion, a cutting edge of the first member of said first pair of cutting members being formed on its exterior surface and a cutting edge of the second member of said first pair of cutting members being formed on its interior surface, the second pair of cutting members being so arranged that a member thereof is located on each side of the longitudinal axis of said first jaw, said second pair of cutting members extending from next adjacent the forward end of said first pair of cutting members and extending towards the front portion of the first jaw, the first member of said second pair of cutting members being longitudinally aligned with the first member of said first pair of cutting members on said first jaw, and the second member of said second pair of cutting members being longitudinally aligned with the second member of said first pair of cutting members on said first jaw, a cutting edge of the first member of said second pair of cutting members being formed on its interior surface, and a cutting edge of the second member of said second pair of cutting members being formed on its exterior surface, whereby the cutting edges on said first members of said first and second pairs and the cutting edges on said second members of said first and second pairs each form substantially continuous cutting surfaces without a lateral offset on said first jaw;

said second jaw having a rear portion and a front portion, and including at least a third pair of cutting members and a fourth pair of cutting members, each cutting member having an interior and an exterior surface, the third pair of cutting members being so arranged that a member thereof is located on each side of the longitudinal axis of said second jaw, said third pair of cutting members extending from the rear portion of the second jaw towards the front portion of the second jaw, but terminating at a forward end short of said front portion, a cutting edge of the first member of said third pair of cutting members being formed on its interior surface and a cutting edge of the second member of said third pair of cutting members being formed on its exterior surface, the fourth pair of cutting members being so arranged that a member thereof is located on each side of the longitudinal axis of said second jaw, said fourth pair of cutting members extending from next adjacent the forward end of said third pair of cutting members and extending towards the front portion of the second jaw, with the first member of said fourth pair of cutting members being longitudinally aligned with the first member of said third pair of cutting members on the second jaw, and the second member of said fourth pair of cutting members being longitudinally aligned with the second member of said third pair of cutting members on the second jaw, a cutting edge of the first member of said fourth pair of cutting members being formed on its exterior surface, and a cutting edge of the second member of said fourth pair of cutting members being formed on its interior surface, whereby the cutting edges on said first members of said third and fourth pairs and the cutting edges on said second members of said third and fourth pairs each form substantially continuous cutting surfaces without a lateral offset on said second jaw; and means for moving at least one of said jaws towards the other said jaw about an axis of rotation so that the respective cutting edges on said first and second jaws may be repositioned from a first position in which the cutting edges on the first jaw are completely disengaged from the cutting edges on the second jaw, to a second position wherein the cutting edges on the first jaw are fully in engagement with the cutting edges on the second jaw, and wherein as said cutting edges are progressively moved from said first towards said second position, the cutting edges on said first pair of cutting members of said first jaw confront and then engage the cutting edges on said third pair of cutting members of said second jaw, and upon further movement of said jaws into the second position the cutting edges on said second pair of cutting members on the first jaw confront and then engage the cutting edges on said fourth pair of cutting members of said second jaw, whereby when the jaws are disposed in said fully engaged position the application of forces in a direction other than to rotate at least one of said jaws about said axis of rotation causes forces to be applied to the cutting members on said first and second jaws in such manner as to urge said members against one another and to maintain said tissue engagement means in a substantially constant position relative to said first and second jaws.

10. The apparatus of claim 9 wherein said means for moving at least one of said first and second jaws towards the other jaw comprises a first pair of parallel arms and a second pair of parallel arms interconnected therewith.

11. The apparatus of claim 9 wherein there are sufficient additional pairs of cutting members on said first and second jaws so that together with said first and second pairs of cutting members on said first jaw, and the third and fourth pairs of cutting members on said second jaw, an enclosed hollow volume is defined when said cutting surfaces are repositioned to their second position wherein all cutting surfaces are fully engaged.

12. An apparatus for cutting and removing a tissue sample from a tissue mass, said apparatus comprising:
- a first jaw with a longitudinal axis having sides which include a rear portion, a frontal cutting edge forming a region adapted to engage said tissue mass, and at least one first incisor, each of said sides of said first jaw being formed of first and second cutting portions which are laterally offset relative to each other and define side cutting edges without a lateral offset; and
- a second jaw with a longitudinal axis having sides which include a rear portion, a frontal cutting edge forming a region adapted to engage said tissue mass, and at least one second incisor, each of said sides of said second jaw being formed of third and fourth cutting portions which are laterally offset relative to each other and define side cutting edges without a lateral offset;
- said first and second jaws being arranged so that either jaw may be pivoted about an axis and said jaws may be repositioned between (i) a disengaged position, and (ii) an engaged position wherein said side cutting edges of said first jaw engage said side cutting edges of said second jaw so as to form a substantially enclosed volume therebetween when said jaws are disposed in said engaged position; and
- said at least one first and said at least one second incisor each comprising a protrusion extending a preselected distance above its associated side cutting edge in said rear portion of its associated jaw such that said at least one first incisor and said at least one second incisor confront and slide over one another so as to be able to engage a tissue mass which may be placed between said incisors before the frontal cutting edges of said first and second jaws engage the same tissue mass when said jaws are repositioned from their disengaged position toward their engaged position.

13. The apparatus of claims 12 wherein said jaws each have additional incisors, and at least one incisor associated with one of said jaws being disposed closer to said axis than at least one incisor associated with the other of said jaws.

14. A dissecting forceps comprising, in combination:
- a first jaw formed of a first and a second wall located one on each side of the longitudinal axis thereof, said walls defining a concave interior region therebetween, the first wall on said first jaw being formed of first and second cutting portions, the first cutting portion being further laterally displaced from said longitudinal axis than said second cutting portion, the second wall on said first jaw being formed of third and fourth cutting portions, the third cutting portion being located laterally closer to said longitudinal axis than said fourth cutting portion, said first through fourth cutting portions defining side cutting edges without a lateral on said first jaw; and
- a second jaw formed of a third and a fourth wall located one on each side of the longitudinal axis thereof, said walls defining a concave interior region therebetween, the third wall on said second jaw being formed of fifth and sixth cutting portions, the fifth cutting portion being located closer to said longitudinal axis than the sixth cutting portion, the fourth wall on said second jaw being formed of seventh and eighth cutting portions, the seventh cutting portion being located laterally further displaced from said longitudinal axis than said eighth cutting portion, said fifth through eighth cutting portions defining side cutting edges without a lateral offset on said second jaw;
- said first and second jaws being arranged so that either jaw may be pivoted about an axis of rotation and said jaws may be repositioned between (i) a disengaged position, and (ii) a fully engaged position, whereby as said jaws are progressively moved towards the fully engaged position, cutting edges of the second and fourth cutting portions on the first jaw engage cutting edges of the sixth and eighth cutting portions on said second jaw, and as said jaws are further moved towards the fully engaged position the cutting edges on the first and third cutting portions of said first jaw engage the cutting edges on the fifth and seventh cutting portions of said second jaw, so as to form a substantially enclosed volume therebetween when said jaws are disposed in said fully engaged position.

15. A surgical instrument, comprising in combination a handle operatively connected to a first and second jaw:
- said first jaw being formed of a first and a second wall located one on each side of the longitudinal axis thereof, the first wall on said first jaw being formed of first and second portions, the first portion being further laterally displaced from said longitudinal axis than said second portion, the second wall on said first jaw being formed of third and fourth portions, the third portion being located laterally closer to said longitudinal axis than said fourth portion, said first through fourth wall portions defining edges on said first jaw without a lateral offset;
- said second jaw being formed of a third and a fourth wall located one on each side of the longitudinal axis thereof, the third wall on said second jaw being formed of fifth and sixth portions, the fifth portion being located closer to said longitudinal axis than said sixth portion, the fourth wall on said second jaw being formed of seventh and eighth portions, the seventh portion being located laterally further displaced from said longitudinal axis than said eighth portion, said fifth through eighth wall portions defining edges on said second jaw without a lateral offset;
- the first and second portions of said first jaw and the seventh and eighth portions of said second jaw terminating in a tip having means for accomplishing a desired surgical task;
- said first and second jaws being arranged so that either jaw may be pivoted about an axis of rotation and said jaws may be repositioned between (i) a disengaged position, and (ii) a fully engaged position, whereby as said jaws are progressively moved towards the fully engaged position, the offset edges of the second and fourth portions on the first jaw engage and slide over the offset edges of the sixth and eighth portions on the second jaw; and as said jaws are further moved towards fully engaged position, the offset edges on the first and third portions of said first jaw engage the offset edges on the fifth and seventh portions of said second jaw to provide a progressively increasing ability of said instrument to prevent misalignment of the tip of said instrument, whereby the means for accomplishing a desired surgical task remains operative regardless of the degree of torsional or sideways force applied to said handle.

16. The apparatus of claim 15 wherein said means for accomplishing a desired surgical task comprises a corrugated gripping member.

* * * * *